(12) United States Patent
Ueno et al.

(10) Patent No.: US 6,823,739 B2
(45) Date of Patent: Nov. 30, 2004

(54) THIN PRESSURE SENSOR AND BIOLOGICAL INFORMATION MEASURING DEVICE USING SAME, AND BIOLOGICAL INFORMATION MEASURING METHOD

(75) Inventors: Naohiro Ueno, Tosu (JP); Morito Akiyama, Tosu (JP); Kiichi Ikeda, Tosu (JP); Hiroshi Tateyama, Tosu (JP)

(73) Assignee: National Institute of Advanced Industrial Science and Technology, Tokyo (JP)

(*) Notice: Subject to any disclaimer, the term of this patent is extended or adjusted under 35 U.S.C. 154(b) by 0 days.

(21) Appl. No.: 10/317,161

(22) Filed: Dec. 12, 2002

(65) Prior Publication Data

US 2003/0115966 A1 Jun. 26, 2003

(30) Foreign Application Priority Data

Dec. 20, 2001 (JP) ........................................ 2001-387001

(51) Int. Cl.[7] .................................................. G01L 9/00
(52) U.S. Cl. ............................. 73/717; 73/721; 73/700
(58) Field of Search ......................... 73/717, 721, 727; 704/270

(56) References Cited

U.S. PATENT DOCUMENTS

| | | | | |
|---|---|---|---|---|
| 5,444,191 A | * | 8/1995 | Yamamoto et al. | ....... 178/18.01 |
| 5,600,197 A | * | 2/1997 | Takeuchi et al. | ............ 310/328 |
| 5,760,675 A | * | 6/1998 | Lee et al. | ...................... 338/2 |
| 5,872,372 A | * | 2/1999 | Lee et al. | .................... 257/254 |
| 5,935,485 A | * | 8/1999 | Tani et al. | ............ 252/62.9 PZ |
| 2002/0072860 A1 | * | 6/2002 | Amano | ......................... 702/19 |
| 2002/0073785 A1 | * | 6/2002 | Prakash et al. | ........ 73/862.041 |
| 2003/0230374 A1 | * | 12/2003 | Yamana et al. | .......... 156/89.12 |

FOREIGN PATENT DOCUMENTS

| | | |
|---|---|---|
| GB | 2 138 144 A | 10/1984 |
| JP | 2000-337971 | 12/2000 |

OTHER PUBLICATIONS

Watanabe et al; "Study on the Non–Restrictive Vital Bio–Measurement by the Air Mattress Methods", T. Sice, vol. 36, No. 11, pp. 894–900, Nov. 2000.

Tanaka; "Unconstrained and Noninvasive Automatic Measurement of Respiration and Heart Rates Using a Strain Gauge"; T. Sice, vol. 36, No. 3, pp. 227–233, Mar. 2000.

"Piezo Film Sensors Technical Manual"; Measurement Specialties, Inc., pp. 1–7.

Ueno et al; "A Foil Type Flexible Pressure Sensor Using Nitelide Aluminum Thin Film"; SICE 2001 in Nagoya, The 40th SICE Annual Conference, Jul. 25–27, 2001.

Ueno et al; "A Study of Flexible Thin Film Pressure Sensor"; SICE S12001, Dec. 20–22, 2001, pp. 361–362.

FlexiForce Sensors—Specifications and Features; http://www.tekscan.com/flexiforce/specs_flexiforce.html.

* cited by examiner

*Primary Examiner*—Edward Lefkowitz
*Assistant Examiner*—Andre Allen
(74) *Attorney, Agent, or Firm*—Nixon & Vanderhye, P.C.; Frank P. Presta

(57) ABSTRACT

A thin pressure sensor includes: a pair of external electrodes, which are respectively made of conductive thin films that are respectively provided with piezoelectric layers on inner sides; and a single internal electrode, made of a conductive thin film, which is sealed between the pair of external electrodes, one of the pair of external electrodes having a conducting window that conducts to said internal electrode. The thin pressure sensor has a simple and thin structure with sufficient durability and mechanical strength.

14 Claims, 4 Drawing Sheets

THIN PRESSURE SENSOR AND BIOLOGICAL INFORMATION MEASURING DEVICE USING SAME, AND BIOLOGICAL INFORMATION MEASURING METHOD

FIELD OF THE INVENTION

The present invention relates to a thin pressure sensor for measuring pressure such as fluid pressure and contact pressure of objects. The invention also relates to a biological information measuring device and a biological information measuring method, using such a thin pressure sensor.

BACKGROUND OF THE INVENTION

Mainstream pressure sensors are adapted to measure deformation of a diaphragm under pressure using a strain gauge or a laser. The applied pressure on the diaphragm is detected from a correlation between the degree of deformation and the pressure. However, in this type of pressure sensor, the diaphragm requires a supporting mechanism and the structure is complex. Accordingly, the thickness of the pressure sensor can only be reduced to several millimeters and it was impossible to achieve a thickness of 0.6 mm or less.

Another type of pressure sensor uses a pressure sensitive material to measure an electric resistance shift that is generated when pressure is applied. A value of the applied pressure is computed from a correlation between the electric resistance and the pressure. This type of pressure sensor does not tolerate a thickness of 100 µm or less because such a thickness impairs durability and mechanical strength.

One application of the pressure measurement is the living body. For example, information of the living body is obtained by measuring changes in pulse, respiration, or body movement of the subject. This is often carried out by measuring changes in pressure of the air-mattress that is placed under the subject laying on his or her back, or by measuring oscillations of wires that are suspended under the pillow. One drawback of such measuring methods, however, is that the sensor can be placed only at particular locations and the methods are only applicable to the living body at rest. In view of such a drawback, there have been attempts to obtain biological information using an ordinary pressure sensor. However, the ordinary pressure sensor is not suitable because it has a hard sensor head, which gives discomfort to the subject.

SUMMARY OF THE INVENTION

The present invention was made in view of the foregoing problems and it is an object of the present invention to provide a novel thin pressure sensor that has a simple and thin structure with sufficient durability and sufficient mechanical strength. Another object of the present invention is to provide a novel biological information measuring device that uses the novel thin pressure sensor of the present invention, and which can solve the drawbacks of conventional biological information measuring devices.

After extensive research on thin pressure sensors and applicability of such pressure sensors to a biological information measuring device, the inventors of the present invention have found that the foregoing objects can be achieved by placing a single internal electrode between a pair of thin film external electrodes that have piezoelectric layers on the inner sides, and by completely shielding the internal electrode from outside between the pair of external electrodes.

Namely, the present invention provides a thin pressure sensor that includes: a pair of external electrodes (1, 1'), which are respectively made of conductive thin films (3, 3') that are respectively provided with piezoelectric layers (2, 2') on inner sides; and a single internal electrode (4), made of a conductive thin film, which is sealed between the pair of external electrodes, one of the pair of external electrodes having a conducting window (5) that conducts to the internal electrode (4). The present invention also provides a biological information measuring device that measures a pressure change of a living body using such a thin pressure sensor. The present invention also provides a biological information measuring method that measures a pressure change of a living body using such a thin pressure sensor.

The present invention thus realizes a thin and highly sensitive pressure sensor. A plurality of such a thin pressure sensor may be provided in the form of a matrix over a flat or curved surface. In this way, a two-dimensional pressure distribution can easily be measured. Further, the thin pressure sensor can be used in direct contact with a living body such as the human body. Further, the thin pressure sensor easily fits non-flat surface shapes of the living body. As a result, biological information, such as pulse, respiration, and body movement, can be measured sensitively in non-restrictive and non-invasive manners.

For a fuller understanding of the nature and advantages of the invention, reference should be made to the ensuing detailed description taken in conjunction with the accompanying drawings.

DESCRIPTION OF THE EMBODIMENTS

The present invention is described below with reference to FIG. 1 through FIG. 8.

Figure 1:
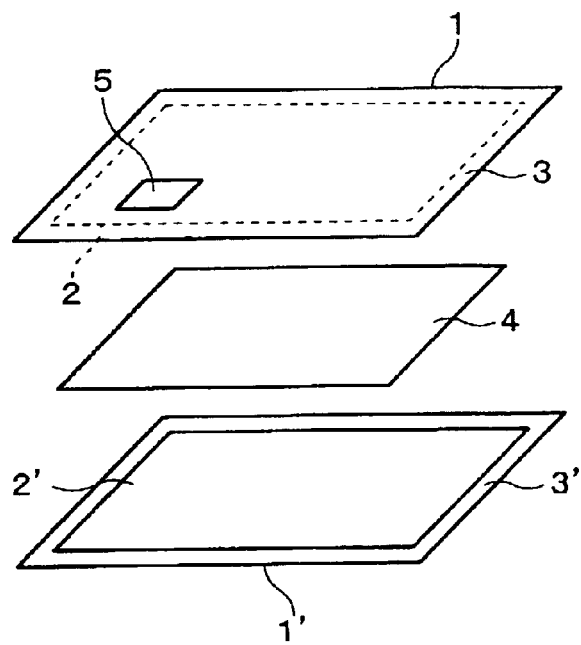
FIG. 1 is an exploded perspective view showing a structure of a thin pressure sensor of the present invention.

FIG. 1 is an exploded perspective view, explaining a structure of a thin pressure sensor of the present invention. The thin pressure sensor includes a pair of external electrodes 1 and 1', a pair of piezoelectric layers 2 and 2', a pair of conductive thin films 3 and 3', and an internal electrode 4. The conductive thin films 3 and 3', which are respectively provided with the piezoelectric layers 2 and 2' on the inner sides, make up the external electrodes 1 and 1', respectively. The internal electrode 4 is a conductive thin film that is completely sealed between the external electrodes 1 and 1'. One of the external electrodes 1 and 1' (external electrode 1 in FIG. 1) has a conducting window 5 that conducts to the internal electrode 4. The conducting window 5 is provided at a suitable portion of the external electrode 1 or 1'. Here, the suitable portion is selected according to use of the thin pressure sensor. Specifically, a central portion of the external electrode is preferably selected when the pressure is applied on the periphery of the thin pressure sensor, and a portion as close as possible to an end of the external electrode is preferably selected when the pressure is applied over the entire surface of the thin pressure sensor.

Figure 2:
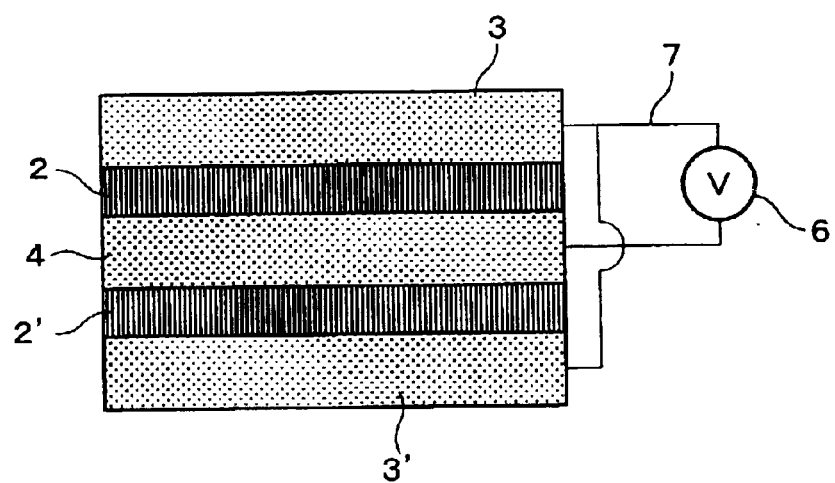
FIG. 2 is a cross sectional view schematically showing a structure of the thin pressure sensor of the present invention.

FIG. 2 is a cross sectional view schematically showing a structure of the thin pressure sensor of the present invention. In addition to the conductive thin films 3 and 3' and the internal electrode 4, there are additionally provided a charge detector 6 and an electrical circuit 7, the electrical circuit 7 being provided between the conductive thin films 3 and 3' and the charge detector 6, and between the internal electrode 4 and the charge detector 6. The charge detector 6 has a charge detecting section that is equipped with an electricity detector, for example, such as an ammeter or a voltmeter.

Applying pressure on a surface of the thin pressure sensor having the foregoing structure causes the internal electrode 4 to generate charge by the piezoelectric effect of the piezoelectric layers 2 and 2'. Here, the quantity of charge generated from the internal electrode 4 is proportional to the magnitude of the applied pressure. In practice, however, a loss such as an internal leak is caused.

Figure 3:
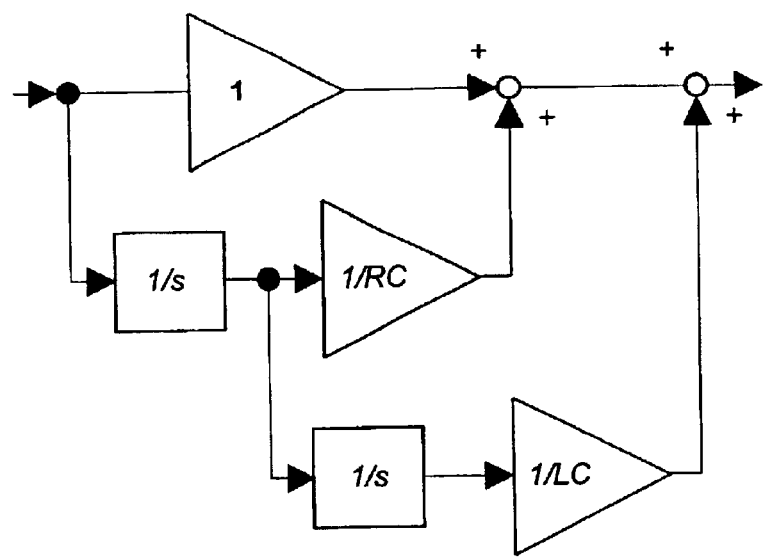
FIG. 3 is a circuit diagram showing a restoring circuit in the thin pressure sensor of the present invention.
Figure 4:
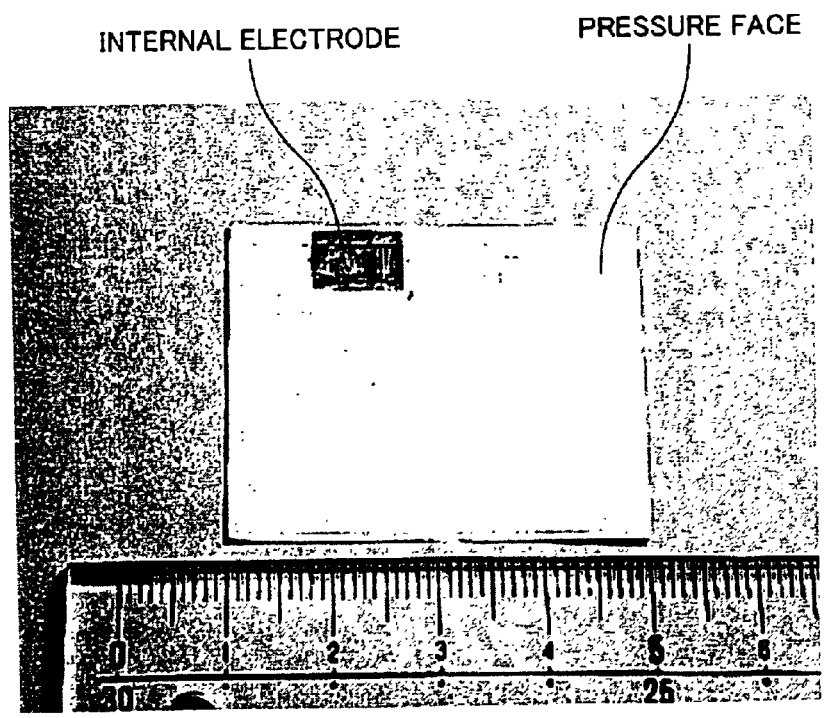
FIG. 4 is an image showing a pressure sensor that is prepared in Examples of the present invention.

FIG. 3 is a circuit diagram showing a restoring circuit (output restoring circuit) that is provided in the thin pressure sensor, and which converts a measured quantity of charge into the original pressure. The restoring circuit has an integrator and a gain, the integrator having parameters of resistance R, capacitance C, and inductance L. In the product device, the restoring circuit may be realized in the form of an electrical circuit or software.

In principle, the pressure sensor with piezoelectric thin films can generally be realized by placing a piezoelectric thin film between a pair of metal foils. However, there is a great difficulty in using such a pressure sensor alone to measure contact pressure, because a leak of charge by contact to the subject is unavoidable when directly measuring contact pressure.

The thin pressure sensor of the present invention has therefore adopted a structure wherein the external electrodes 1 and 1' surround the internal electrode 4 so as to completely shield the internal electrode 4 from outside. In addition, the external electrodes 1 and 1' are grounded. This completely eliminates a leak of charge from the internal electrode 4 to the subject that is in contact with the sensor, thereby fully realizing the function of the contact pressure sensor.

The thin pressure sensor of the present invention excels in sensitivity by the provision of the piezoelectric elements 3 and 3' on the both sides of the internal electrode 4, because the amount of charge generated from such a structure is two times that from the structure in which the piezoelectric thin film is placed between a pair of metal foils.

It is preferable that the conductive thin films and the piezoelectric layers of the thin pressure sensor of the present invention are made of a flexible material and are individually deformable as a whole. In this way, even a slight pressure change on a non-flat contact face, such as the skin surface of a living body, can be measured.

The conductive thin films used for the external electrodes 1 and 1' and the internal electrode 4 of the thin pressure sensor of the present invention may be made of a metal such as copper, silver, gold, platinum, tin, and aluminum. Among these metals, aluminum is preferable because it is inexpensive and light-weight. The conductive thin films are generally prepared as a foil with a thickness of 5 $\mu$m to 50 $\mu$m, or more preferably 10 $\mu$m to 30 $\mu$m. In this way, a thin sensor can be realized while maintaining mechanical strength. Other than metals, carbon is also suitable for the conductive thin films.

The piezoelectric layers 2 and 2' of the conductive thin films 3 and 3' may be, for example, ceramic piezoelectrics such as barium titanate, lead zirconate titanate (PZT), and aluminum nitride, or polymer piezoelectrics such as a polyvinylidene fluoride polymer, a polyvinylidene fluoride co-polymer, and a vinylidene cyanide co-polymer. Of these piezoelectrics, those made of an inorganic material such as ceramic is preferable because they do not decompose even when used for extended periods of time and they have a desirably linear sensitivity.

The piezoelectric layers 2 and 2' may be formed on the surfaces of the external electrodes by any of the conventional methods that are used to form piezoelectric layers on metal substrates. Examples of such conventional methods include a sputtering method, a coating method, a chemical vapor deposition method, a vacuum vapor deposition method, an ion plating method, and a plating method. The piezoelectric layer is generally formed in a thickness of 0.5 $\mu$m to 10 $\mu$m, or more preferably 1 $\mu$m to 5 $\mu$m. In this way, insulating characteristics can be improved while reducing the time to form the piezoelectric layers.

Preferably, the thin pressure sensor of the present invention, with the foregoing conductive thin films and piezoelectric layers, has a thickness of 50 $\mu$m or less. In this way, flexibility can be sustained while maintaining mechanical strength.

The thin pressure sensor of the present invention can be brought into direct contact with a conductor such as the living body. Further, the sensitivity of the thin pressure sensor can be increased by increasing the pressure face area. These characteristics enable the thin pressure sensor to capture a pressure change on a skin surface of the living body. That is, biological information can be detected by measuring changes in pressure that are induced by a pulse, respiration, or body movement of the subject. Thus, with the thin pressure sensor, a biological information measuring device that detects biological information can be realized. Note that, the body movement includes turning over while one is asleep, or unconscious movement of arms or feet, for example.

The biological information measuring device so prepared is thin and flexible and therefore can be used to measure a pressure change on a living body surface by being incorporated in a cloth or in contact with the body either directly or via a piece of cloth. Detecting biological information with the biological information measuring device is advantageous because a state of pulse or respiration can be detected without giving discomfort to the subject and even when the subject is moving.

A measurement error can be reduced by increasing the pressure face area of the thin pressure sensor to the size of about 30 mm×30 mm. A pressure face area of this size is enough to cover misalignment of the pressure face area with the site of a pressure change on the body surface. Thus, the thin pressure sensor should preferably have a pressure face area of no smaller than 30 mm×30 mm. This enables the sensor to be positioned in close proximity with the body surface and provides a large contact area in conformity with the body shape. As a result, highly sensitive and highly accurate measurements can be realized.

A biological information measuring method of the present invention uses the foregoing thin pressure sensor to measure a pressure change of the living body. With this method, biological information, such as pulse, respiration, and movement of the living body can be measured sensitively in non-restrictive and non-invasive manners.

The thin pressure sensor may be provided in a matrix form over the entire surface of bedding such as a sheet, a futon, or a blanket. In this way, changes in pressure at various parts of a moving subject can be captured. In addition, it becomes easier to detect movement of the subject.

The present invention is described below in more detail by way of Examples. It should be noted that the present invention is not limited in any ways by the following Examples.

EXAMPLE 1

First, external electrodes were prepared. An aluminum foil of 12 µm thick was cut into pieces, each measuring 30 mm in length and 40 mm in width. On one side of each piece was formed a layer of a highly oriented aluminum nitride thin film, 26 mm long, 36 mm wide, and 1 µm thick, by sputtering.

Two of the external electrodes so prepared were stacked on their aluminum nitride layer sides. An aluminum foil (26 mm×36 mm, 12 µm thick) was slid into a spacing between the external electrodes and sealed therein. Thereafter, a conducting window, 5 mm long and 8 mm wide, was formed through the upper external electrode. The result was the thin pressure sensor shown in the image of FIG. 4. The total thickness of this thin pressure sensor was 38 µm.

Figure 5:
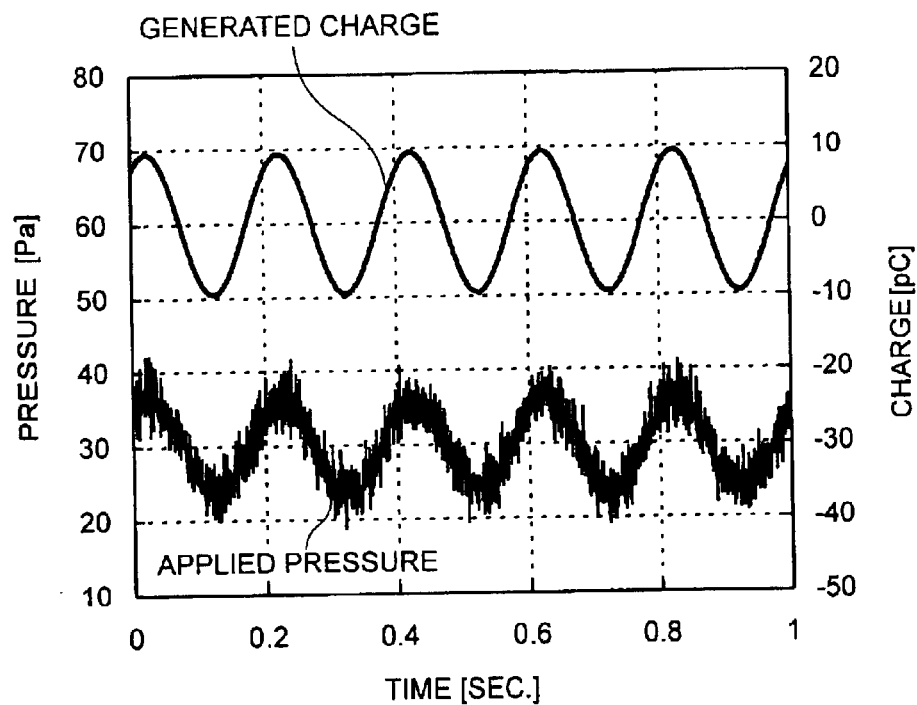
FIG. 5 is a graph showing changes in output of the pressure sensor of the Example and changes in applied pressure in the form of a sinusoidal wave as a function of time.

The amount of charge generated by the thin pressure sensor was measured as a voltage, using a charge amplifier. The result of measurement is shown in the graph of FIG. 5, which indicates changes in applied pressure [Pa] and changes in output of the charge amplifier (charge [pC]) as a function of time.

Figure 6:
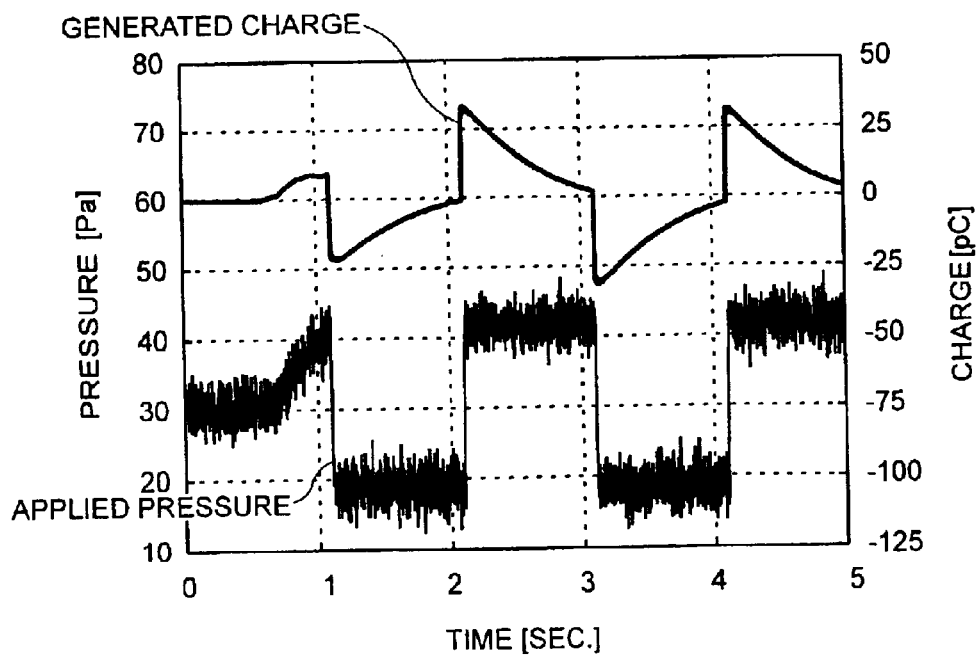
FIG. 6 is a graph showing changes in output of the pressure sensor of the Example and changes in applied pressure in the form of a square wave as a function of time.
Figure 7:
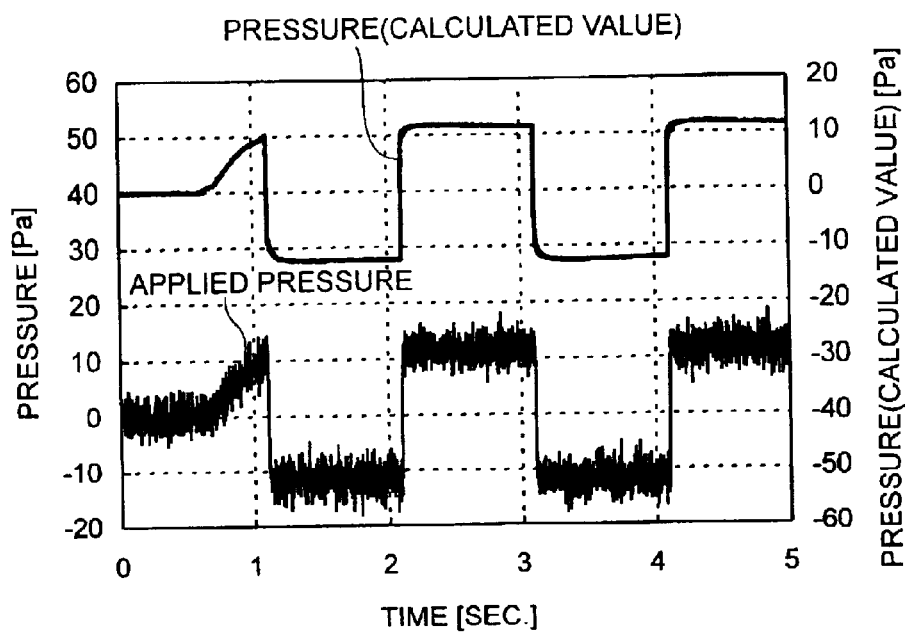
FIG. 7 is a graph showing changes in output of a restoring circuit in the pressure sensor of the Example and changes in applied pressure in the form of a square wave as a function of time.

FIG. 6 is a graph showing changes in applied pressure [Pa] and changes in output of the charge amplifier (charge [pC]) in the form of a square wave as a function of time. It can be seen from FIG. 6 that the generated charge attenuates by the internal leak under constant applied pressure. FIG. 7 is a graph showing changes in applied pressure [Pa] and changes in output of a restoring circuit with a measured resistance, capacitance, and inductance (pressure (calculated value) [Pa]) as a function of time. It can be seen from FIG. 7 that the output of the restoring circuit restores portions of the applied pressure.

EXAMPLE 2

Figure 8:
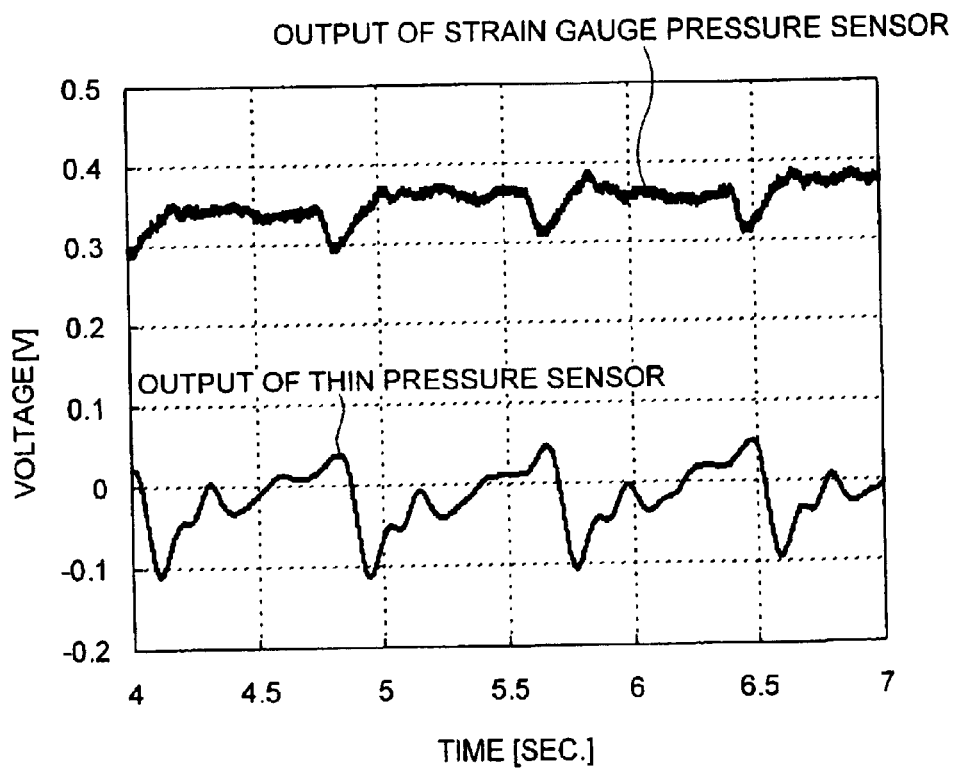
FIG. 8 is a graph showing changes in output of the pressure sensor measuring pulses of a human body as a function of time.

A thin pressure sensor that was prepared in the same manner as in Example 1 was attached to a flexible supporter and fastened on the ankle of the subject to measure pulses. The result of measurement is shown in FIG. 8, which indicates changes in output of the pressure sensor as a function of time, together with changes in pressure on the body surface of the subject's neck, which was obtained by measuring pulses of the carotid artery using a commercially available small pressure sensor of the strain gauge type. It can be seen from FIG. 8 that even small pulses, which could not be captured conventionally, can be detected.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A thin pressure sensor comprising:
   a pair of first electrodes, which are respectively made of conductive thin films that are respectively provided with piezoelectric layers on inner sides; and
   a single second electrode, made of a conductive thin film, which is completely surrounded and sealed by said pair of first electrodes,
   said second electrode, surrounded by said pair of first electrodes, being completely isolated from outside, and
   one of said pair of first electrodes having a conducting window that conducts to said second electrode.

2. The thin pressure sensor as set forth in claim 1, wherein the conductive thin film and the piezoelectric layer are made of a flexible material and are individually deformable as a whole.

3. The thin pressure sensor as set forth in claim 1, wherein the conductive thin film is a thin film of a metal.

4. The thin pressure sensor as set forth in claim 3, wherein the metal is selected from the group consisting of copper, silver, gold, platinum, tin and aluminum.

5. The thin pressure sensor as set forth in claim 1, wherein the conductive thin film is a thin film of carbon.

6. The thin pressure sensor as set forth in claim 1, wherein the piezoelectric layer of the conductive thin film is a thin film of a ceramic piezoelectric or a thin film of a polymer piezoelectric.

7. The thin pressure sensor as set forth in claim 6, wherein the ceramic piezoelectric is selected from the group consisting of barium titanate, lead zirconate titanate (PZT), and aluminum nitride.

8. The thin pressure sensor as set forth in claim 6, wherein the polymer piezoelectric is selected from the group consisting of a polyvinylidene fluoride polymer, a polyvinylidene fluoride co-polymer, and a vinylidene cyanide co-polymer.

9. The thin pressure sensor as set forth in claim 1, wherein the thin pressure sensor has a thickness of 50 µm or less.

10. The thin pressure sensor as set forth in claim 1, further comprising an output restoring circuit.

11. The thin pressure sensor as set forth in claim 1, wherein the conductive thin film has a thickness in a range of from 10 µm to 30 µm.

12. The thin pressure sensor as set forth in claim 1, wherein the piezoelectric layer has a thickness in a range of from 1 µm to 5 µm.

13. A biological information measuring method, comprising the step of measuring a pressure change of a living body using a thin pressure sensor,
   the thin pressure sensor including:
   a pair of first electrodes, which are respectively made of conductive thin films that are respectively provided with piezoelectric layers on inner sides; and
   a single second electrode, made of a conductive thin film, which is completely surrounded and sealed by said pair of first electrodes,
   said second electrode, surrounded by said pair of first electrodes, being completely isolated from outside, and
   one of said pair of first electrodes having a conducting window that conducts to said second electrode.

14. The biological information measuring method as set forth in claim 13, wherein the measured pressure change is a pulse, respiration, or body movement.

* * * * *